United States Patent [19]

Ozawa et al.

[11] 4,093,670
[45] June 6, 1978

[54] PROCESS OF ISOMERIZING OLIGOMERS OF HEXAFLUOROPROPENE

[76] Inventors: Masahiro Ozawa, No. 1-6-8, Minami-dai, Kami-fukuoka City; Tadaaki Komatsu, No. 271-8, Fujikubo, Miyoshi-cho, Iruma-gun, Saitama Prefecture; Kimiaki Matsuoka, No. 3-35-7, Kishi-machi, Kawagoe City, all of Japan

[21] Appl. No.: 764,652

[22] Filed: Feb. 1, 1977

[30] Foreign Application Priority Data

Mar. 5, 1976  Japan ................................ 51-23142

[51] Int. Cl.² ............................................. C07C 21/18
[52] U.S. Cl. ........................... 260/653.1 R; 260/653.3
[58] Field of Search ........................... 260/653.1, 653.3

[56] References Cited

PUBLICATIONS

Ishikawa et al. (I), Chemical Abstracts; 78, 57656h.
Ishikawa et al. (II), Chemical Abstracts, 83, 163550g.
Martini et al., Tetrahedron Letters No. 24, pp. 2129-2132, 1974.

*Primary Examiner*—C. Davis
*Attorney, Agent, or Firm*—Fleit & Jacobson

[57] ABSTRACT

Easy-to-prepare dimers of hexafluoropropene such as

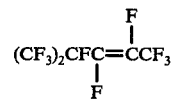

are heated at 20°–150° C in a nonprotonic polar solvent such as acetonitrile in the presence of an alkali metal fluoride and a crown ether to isomerize the dimers into thermodynamically stable

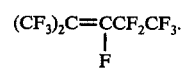

This process is applicable also to the isomerization of trimers such as

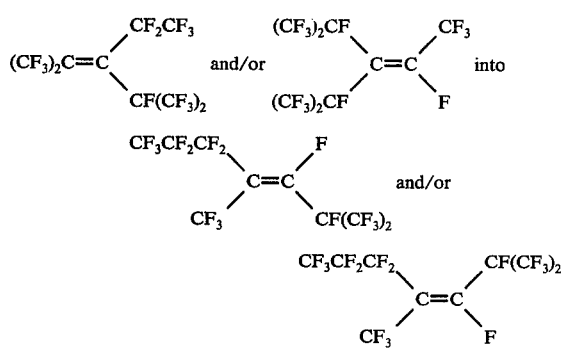

25 Claims, No Drawings

PROCESS OF ISOMERIZING OLIGOMERS OF HEXAFLUOROPROPENE

This invention relates to oligomers of hexafluoropropene, and more particularly to a process of isomerizing dimers and/or trimers of hexafluoropropene respectively into thermodynamically stable isomers thereof.

Oligomers of hexafluoropropene are known to be useful both as thermally and chemically stable solvents and as intermediates for the preparation of fluorine-containing surfactants and water repellants. Usually, oligomerization of hexafluoropropene monomer gives an oligomer mixture containing dimers and trimers of the following formulas.

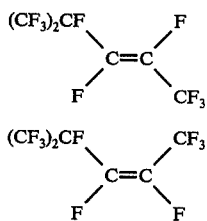

(The subscripts $t$ and $c$ indicate trans form and cis form, respectively.)

Trimers:

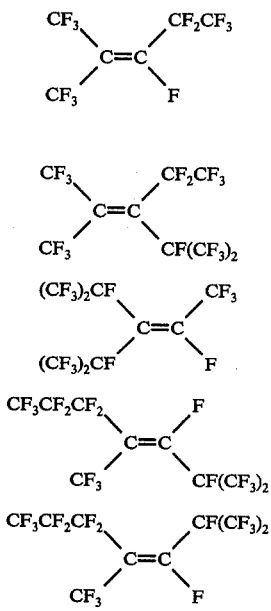

For example, an oligomer mixture obtained by oligomerizing hexafluoropropene monomer in N, N-dimethylformamide(30 ml) at 30° C in the presence of potassium fluoride (0.29 g) as a catalyst is usually composed of about 33% of dimer (IIA)$_t$, about 12% of dimer (IIB), about 25% of trimer (IIIA), about 29% of trimer (IIIB) and about 1% of trimer (IIIC) by weight.

These isomers have different uses since they are different from one another in solubility in organic solvents and chemical stability, particularly reactivity to nucleophilic reagents. It is desired, therefore, that these isomers be obtained not as a mixture with an uncontrollable composition but as individual isomers optionally chosen according to an intended use or as a mixture the most part of which is a desired isomer. Among the above oligomers, the dimer (IIB) and the trimer (IIIC) are of greater use than the others because of higher thermodynamic stability and chemical reactivity. For example, the dimer (IIB) gives perfluorohexynylphenyl ether, which is an important intermediate in the production of surfactants, by reaction with phenol in the presence of triethylamine as a condensation reagent.

Japanese Patent Application Disclosure No. 50(1975)-117705 discloses a process of isomerizing the dimer (IIA)$_t$ into (IIB) by heating the former dimer (IIA)$_t$ in sulfolane using a catalyst such as KF. A process of heating the trimer (IIIA) or (IIIB) in dimethylformamide using KHF$_2$ as a catalyst to isomerize it into the isomer (IIIC) is shown in Chem. Commun. 1444(1970). Including these processes, hitherto proposed processes of isomerizing hexafluoropropene oligomers commonly require the employment of high heating temperatures above 100° C and long reaction time at such high temperatures.

It is an object of the present invention to provide a process of isomerizing dimers and trimers of hexafluoropropene respectively into thermodynamically stable isomers (IIB) and (IIIC), which process can be performed at comparatively low temperatures and completed in comparatively small amounts of time.

A process according to the invention comprises the steps of (a) preparing a mixture of a non-protonic polar solvent, an alkali metal fluoride, a crown ether and at least one of the above defined isomers (IIA)$_t$, (IIA)$_c$, (IIIA) and (IIIB), and (b) heating the mixture at a temperature in the range from 20° to 150° C.

When the preparation of the dimer (IIB) is desired, the heating step is performed preferably at a temperature of 40°-70° C. To prepare the trimer (IIIC), the heating step is performed preferably at 60°-100° C. The heating step is accomplished at atmospheric pressure but may alternatively be performed at elevated pressures.

Prior to the present invention, we have proposed an improved process of preparing oligomers of hexafluoropropene (hereinafter referred to as HFP), which process is primarily characterized by the use of a combination of an alkali metal halide, particularly fluoride, and a crown ether to cause oligomerization of HFP monomer in a non-protonic polar solvent. This process is disclosed in our prior application, Ser. No. 676,494, filed Apr. 13, 1976, now U.S. Pat. No. 4,042,638. The alkali metal halide and the crown ether form a complex in the solvent, and the complex serves as an oligomerization catalyst, so that the oligomerization can be achieved at relatively low temperatures and low pressures.

We have discovered that a complex of a crown ether with an alkali metal fluoride can catalyze also the isomerization of HFP oligomers into the dimer (IIB) or the trimer (IIIC) without needing rigorous reaction conditions.

Preferred examples of alkali metal fluorides for use in the isomerization process according to the invention are potassium fluoride and cesium fluoride.

In the present invention, "crown ether" includes every macrocyclic ether (its oxygen atoms may at least partially be substituted by nitrogen, sulfur and/or phosphorus) which has the property of strongly coordinating the cation of a dissociable compound such as an alkali metal halide into its hole and, as a result, activating the corresponding anion to exhibit a high catalytic activity. The dissociation of an alkali metal fluoride will be promoted by the cation-coordinating or trapping activity of a crown ether, causing the anion of the alkali metal fluoride to exhibit an enhanced nucleophilic tendency. This is considered a fundamental reason for the remarkable catalytic ability of a complex-forming combination of an alkali metal fluoride and a crown ether. Accordingly it is preferable to employ a crown ether having a hole diameter optimum to coordinate the cation of the employed alkali metal fluoride.

Practical examples of useful crown ethers are:

(A) a group of cyclic polyethers such as, according to the simplified nomenclature by Pedersen et al, J. of Am. Chem. Soc., Vol. 89, 7017–36 (1967), decalyl-15-crown-5, dibenzo-14-crown-4, dibenzo-20-crown-4, dibenzo-18-crown-5, 18-crown-6, dibenzo-18-crown-6, benzo-15-crown-5, dicyclohexyl-18-crown-6 and dibenzo-26-crown-6;

(B) a group of substituted polyethers which are given by partially or entirely substituting the oxygen atoms of the cyclic polyethers (A) by sulfur, and (C) a group of compounds expressed by the following general formula

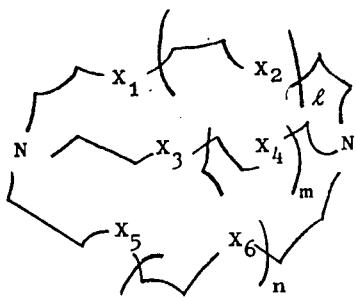

where $X_1$, $X_2$, $X_3$, $X_4$, $X_5$ and $X_6$ represent independently O, S or R-N(R represents an alkyl group having 1 to 5 carbon atoms), and subscripts $l$, $m$ and $n$ represent independently an integer from 1 to 5.

Preferred examples of non-protonic polar solvents for a process according to the invention are acetonitrile, N,N-dimethylformamide and dimethyl sulfoxide. Practically, the use of acetonitrile is convenient.

The isomerization according to the invention can be made to proceed at an augmented rate of reaction by increasing the amount of the catalyst. When economical consideration is also taken, it is preferable that the alkali metal fluoride amounts to 0.1 –10 mol/liter of the solvent and that the crown ether is present in an amount of at least 2 mol% of the alkali metal fluoride.

The temperature for the isomerization can optionally be settled between about 20° C and 150° C. However, a narrower range from 40° to 70° C is preferable for isomerizing the dimer (IIA)$_t$ into the isomer (IIB) and a different range of 60° – 100° C is preferable for isomerizing the trimers (IIIA) and/or (IIIB) into (IIIC)$_a$ and/or (IIIC)$_b$. It is undesirable to employ temperatures above 150° C because of the solvent being decomposed and/or the aforementioned complex losing stability. The heating for the isomerization can be performed at atmospheric pressure, but the employment of pressures of up to about 10 kg/cm² (in gage pressure) is possible.

Oligomers of HFP to be isomerized according to the invention may be prepared by any known process. An oligomer mixture containing any combination of the isomers (IIA)$_t$, (IIA)$_c$, (IIIA) and (IIIB) can be used as the starting material for the process according to the invention. (It is permissible that the starting mixture contains certain amounts of isomers (IIB) and/or (IIIC) too.) Alternatively, any one of these isomers (IIA)$_t$, (IIA)$_c$, (IIIA) and (IIIB) may singly be used preceded by an isolation procedure. It is possible to perform the oligomerization of HFP and the isomerization of the oligomer in a continuous way. In this case, HFP monomer is oligomerized to the dimers and/or the trimers in the above described non-protonic polar solvent by the use of the described alkali metal fluoride and crown ether at a temperature below the isomerization temperature, for example around 0° C. After the completion of the oligomerization process, the temperature of the reaction system is raised, for example, to 40°–100° C in order that the isomerization according to the invention takes place. This method is particularly convenient to the preparation of the isomer (IIB) from the monomer of HFP with high yield.

The process according to the invention is advantageous over conventional isomerization processes in that a thermodynamically stable isomer such as the dimer (IIB) or the trimer (IIIC) can be obtained through an isomerization reaction which proceeds under mild reaction conditions and is completed in a short reaction time. The invention will be illustrated by the following Examples. Several References will also be presented for the sake of comparison.

EXAMPLE 1

In this example, the dimer (IIA)$_t$ was isomerized into the isomer (IIB). A Kjeldahl flask with a volumetric capacity of 20 ml was used as a reaction vessel. At first, 10 ml of acetonitrile was poured into the the flask to which was added with 0.0145 g (0.00025 mol) of KF and 0.065 g (0.00025 mol) of 18-crown-6. Then the flask was tightly plugged and placed in a water bath maintained at 40° C with the precision of ±0.2° C. The mixture in the flask was agitated by a magnetic stirrer for 30 min under this condition. Then 3 g of an oligomer mixture of HFP was introduced into the flask, and the temperature of the reaction system was kept at 40° C. This oligomer mixture consisted of 96.27 Wt% of the dimer (IIA)$_t$ and 3.73 Wt% of the dimer (IIB). After 3 hr, the composition of an oligomer phase in the flask was analyzed by gas chromatography. The result is presented in the following Table 1 in terms of isomerization rate, k%, defined by the following equation.

$$k = \frac{\{P_1 \text{ of (IIA)}_t\} - \{P_2 \text{ of (IIA)}_t\}}{\{P_1 \text{ of (IIA)}_t\}} \times 100$$

where $P_1$ is the initial amount (mol%) of the isomer (IIA)$_t$ in the oligomer mixture subjected to the isomerization, and $P_2$ is the amount (mol%) of the same component at the moment of the analysis.

EXAMPLES 2–8

These examples were identical with Example 1 except that the quantity of KF, the quantity of the crown ether and/or the kind of the crown ether were varied as shown in the following Table together with the results.

| Example No. | Catalyst | | Rate of isomerization, k (mol%) |
|---|---|---|---|
| | KF (mol) | Crown ether (mol) | |
| 1 | 0.00025 | 18-crown-6 | 90.1 |

-continued

| Example No. | Catalyst KF (mol) | Crown ether (mol) | Rate of isomerization, k (mol%) |
|---|---|---|---|
| 2 | 0.00125 | 18-crown-6 0.00025 | 88.3 |
| 3 | 0.00025 | 18-crown-6 0.0005 | 95.9 |
| 4 | 0.0005 | 18-crown-6 0.0005 | 99.3 |
| 5 | 0.0025 | 18-crown-6 0.0005 | 99.0 |
| 6 | 0.00125 | benzo-15-crown-5 0.00025 | 40.0 |
| 7 | 0.00125 | dibenzo-18-crown-6 0.00025 | 81.2 |
| 8 | 0.00125 | dicyclohexyl-18-crown-6 0.00025 | 90.5 |

REFERENCE 1

Example 2 was repeated [using 0.073 g (0.00125 mol) of KF] except that the addition of 18-crown-6 was omitted.

After the lapse of 3 hr from the introduction of the HFP oligomer mixture, the analysis revealed that the rate of isomerization, k, was zero.

REFERENCE 2

This reference relates to the preparation of an oligomer mixture of HFP according to a process disclosed in our prior application referred to hereinbefore.

In a 100 ml pressure-proof reaction tube of glass, 0.29 g (0.005 mol) of KF and 0.26 g (0.001 mol) of 18-crown-6 were added to 30 ml of acetonitrile. Then the interior of the reaction tube was cooled to −78° C and evacuated. After that the reaction tube was maintained in an ice bath for 30 min. Then 15 g of HFP monomer was introduced into the reaction tube at such flow rate that the pressure in the reaction tube remained at 1.5–2.0 kg/cm² in gage pressure. During this procedure the reaction system in the tube was agitated by a magnetic stirrer. After 30 min from the completion of the charging of HFP, an oligomer mixture was separated from the reaction system by the use of a separating funnel. This oligomer mixture weighed 14.0 g (93.6% yield), and gas chromatography analysis gave the following composition by weight: 94.4% dimer (IIA)$_t$, trace of dimer (IIA)$_c$, 3.6% dimer (IIB), 0.6% trimer (IIIA), 0.7% trimer (IIIB) and 0.7% trimer (IIIC).

EXAMPLE 9

Successively to the procedures of Reference 2, the temperature of the reaction system was raised to 50° C using a hot water bath, and this temperature was maintained for 3 hr thereafter to cause isomerization of the HFP oligomers. As a result, 13.0 g of HFP oligomer mixture was separated from the reaction system, meaning 90% yield (based on the used monomer). Gas chromatographic anaylsis gave the following composition by weight: 3.35% dimer (IIA)$_t$, trace of dimer (IIA)$_c$, 93.26% dimer (IIB), 2.06% trimer (IIIA) and 1.24% trimer (IIIB).

EXAMPLE 10

A mixture of HFP trimers (IIIA) (63 wt%) and (IIIB) (37 wt%), 3 g in total, was introduced into a mixture of 10 ml of acetonitrile, 0.073 g(0.00125 mol) of KF and 0.066 g(0.00025 mol) of 18-crown-6. The entire reaction system was kept at 70° C for 20 hr to cause isomerization. Gas chromatographic analysis of the resultant oligomer phase revealed the following composition by weight: 3.26% dimer (IIB), 46.16% trimer (IIIA), 28.15% trimer (IIIB) and 22.43% trimer (IIIC).

REFERENCE 3

Example 10 was repeated except that the use of 18-crown-6 was omitted. It was analytically confirmed that the starting mixture of the trimers (IIIA) and (IIIB) remained with the same composition: no isomerization had occurred.

What is claimed is:

1. A process of isomerizing oligomers of hexafluoropropene into a thermodynamically stable isomer, comprising the steps of:

preparing a mixture of non-protonic polar solvent, an alkali metal fluoride, a crown ether and at least one of the following dimers and trimers of hexafluoropropene;

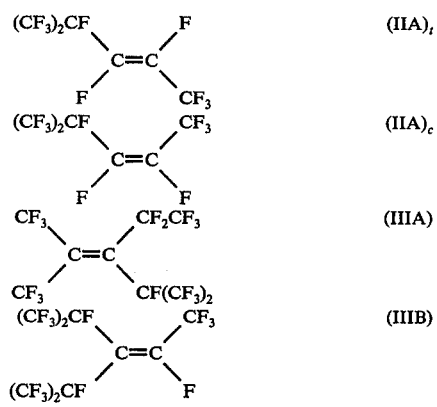

and heating the mixture at a temperature in the range from 20 to 150° C, whereby said dimers and trimers are isomerized respectively into a dimer having the formula (IIB)

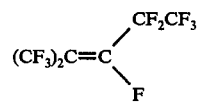

and a trimer having the formula (IIIC)$_a$

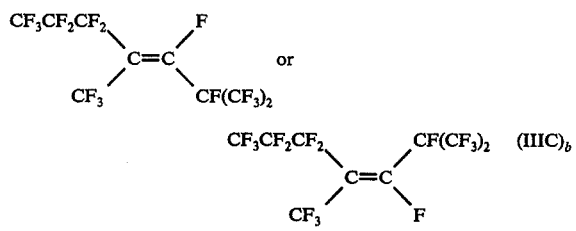

2. A process as claimed in claim 1, wherein said non-protonic polar solvent is selected from the group consisting of acetonitrile, N, N-dimethylformamide and dimethyl sulfoxide, said alkali metal fluoride is selected from the group consisting of potassium fluoride and cesium fluoride, and said crown ether is a cyclopolyether selected from the group consisting of 18- crown-6, benzo-15-crown-5, dibenzo-18-crown-6, dicyclohexyl-18-crown-6, decalyl-15-crown-5, dibenzo-14-crown-4, dibenzo-20-crown-4, dibenzo-18-crown-5, and dibenzo-26-crown-6, including their derivatives given by at least partially substituting the oxygen atoms thereof by sulfur.

3. A process as claimed in claim 2, wherein the amount of said alkali metal fluoride in said mixture relative to said solvent is in the range from 0.1 to 10 mol/liter, and the amount of said crown ether in said mixture is at least 2 mol% of said alkali metal fluoride.

4. A process as claimed in claim 3, wherein the heating step is performed at atmospheric pressure.

5. A process as claimed in claim 3, wherein the heating step is performed at a pressure above atmospheric pressure but below about 10 kg/cm² in gage pressure.

6. A process as claimed in claim 3, wherein said mixture is prepared by oligomerizing hexafluoropropene monomer in said solvent in the presence of said alkali metal halide and said crown ether at a temperature below said temperature at the heating step.

7. A process as claimed in claim 1, wherein said crown ether is a compound expressed by the general formula

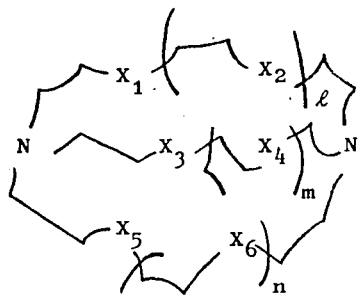

where $X_1$, $X_2$, $X_3$, $X_4$, $X_5$ and $X_6$ represent individually O, S or R-N, R representing an alkyl group having 1 to 5 carbon atoms, and the subscripts $l$, $m$ and $n$ represent individually an integer from 1 to 5.

8. A process of isomerizing an oligomer of hexafluoropropene containing at least one of hexafluoropropene dimers

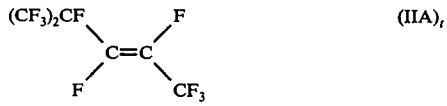 (IIA)$_t$ and

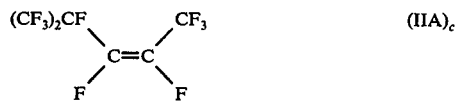 (IIA)$_c$ into an isomer

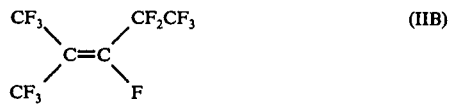 (IIB)

comprising the steps of:
preparing a mixture of a non-protonic polar solvent, an alkali metal fluoride, a crown ether and an oligomer of hexafluoropropene containing at least one of said dimers (IIA)$_t$ and (IIA)$_c$; and
heating said mixture at a temperature in the range from 40° to 70° C.

9. A process as claimed in claim 8, wherein said non-protonic polar solvent is selected from the group consisting of acetonitrile, N, N-dimethylformamide and dimethyl sulfoxide, said alkali metal fluoride is selected from the group consisting of potassium fluoride and cesium fluoride, and said crown ether is a cyclic polyether selected from the group consisting of 18-crown-6, benzo-15-crown-5, dibenzo-18-crown-6, dicyclohexyl-18-crown-6, decalyl-15-crown-5, dibenzo-14-crown-4, dibenzo-20-crown-4, dibenzo-18-crown-5, and dibenzo-26-crown-6, the amount of said alkali metal fluoride in said mixture relative to said solvent being in the range from 0.1 to 10 mol/liter, and the amount of said crown ether in said mixture being at least 2 mol% of said alkali metal fluoride.

10. A process of isomerizing at least one of the hexafluoropropene trimers

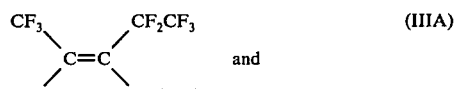 (IIIA)

and

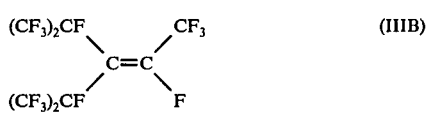 (IIIB)

into at least one of the trimers

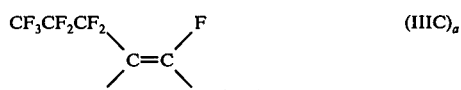 (IIIC)$_a$ and

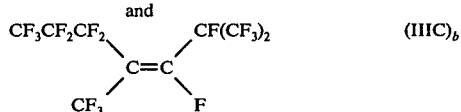 (IIIC)$_b$ comprising the steps of:
preparing a mixture of a non-protonic polar solvent, an alkali metal fluoride, a crown ether and an oligomer of hexafluoropropene containing at least one of said trimers (IIIA) and (IIIB); and
heating said mixture at a temperature in the range from 60 to 100° C.

11. A process as claimed in claim 10, wherein said non-protonic polar solvent is selected from the group consisting of acetonitrile, N,N-dimethylformamide and dimethyl sulfoxide, said alkali metal fluoride is selected from the group consisting of potassium fluoride and cesium fluoride, and said crown ether is a cyclic polyether selected from the group consisting of 18-crown-6, benzo-15-crown-5, dibenzo-18-crown-6, dicyclohexyl-18-crown-6, decalyl-15-crown-5, dibenzo-14-crown-4, dibenzo-20-crown-4, dibenzo-18-crown-5 and dibenzo-26-crown-6, the amount of said alkali metal fluoride in said mixture relative to said solvent being in the range from 0.1 to 10 mol/liter, and the amount of said crown ether in said mixture being at least 2 mol% of said alkali metal fluoride.

12. A process as claimed in claim 1, wherein the temperature of heating the mixture ranges from about 40° to 100° C.

13. A process as claimed in claim 8 wherein the mixture contains a substantial amount of dimer (IIA)$_t$.

14. A process as claimed in claim 9, wherein the heating step is performed at atmospheric pressure.

15. A process as claimed in claim 9, wherein said mixture is prepared by oligomerizing hexafluoropropene monomer in said solvent in the presence of said alkali metal halide and such crown ether at a temperature below said temperature at the heating step.

16. A process of converting an oligomer of hexafluoropropene into a thermodynamically stable isomer thereof, comprising:
(a) preparing a mixture containing a nonprotonic polar solvent, an alkali metal fluoride, a crown ether, and at least one member selected from the group consisting of dimer (IIA)$_t$ having the formula

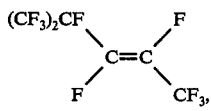

dimer (IIA)$_c$ having the formula

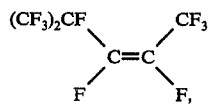

trimer (IIIA) having the formula

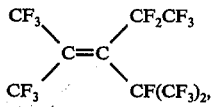

and trimer (IIIB) having the formula

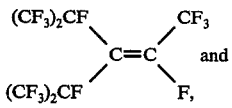

(b) heating the mixture at a temperature of about from 20° C to 150° C, whereby dimers (IIA)$_t$ and (IIA)$_c$, where present, are each converted into the thermodynamically stable dimeric osomer (IIB) having the formula

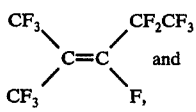

trimers (IIIA) and (IIIB), where present, are respectively converted into the thermodynamically stable trimeric isomers (IIIC)$_a$ and (IIIC)$_b$ having the respective formulas

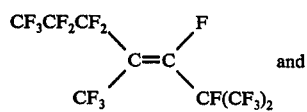

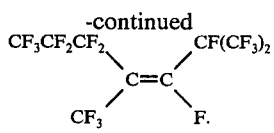

17. The process of claim 16 wherein the nonprotonic polar solvent is a member selected from the group consisting of acetonitrile, N,N-dimethylformamide, and dimethyl sulfoxide.

18. The process of claim 16 wherein the alkali metal fluoride is a member selected from the group consisting of potassium fluoride and cesium fluoride.

19. The process of claim 16 wherein the crown ether is a member selected from the group consisting of
(a) a polycyclic ether selected from the group consisting of 18-crown-6, benzo-15-crown-5, dibenzo-18-crown-6, dicyclohexyl-18-crown-6, decalyl-15-crown-5, dibenzo-14-crown-4, dibenzo-20-crown-4, dibenzo-18-crown-5, and dibenzo-26-crown-6;
(b) the polycyclic ethers of (a) above, in which the oxygen atoms have been at least partially replaced by sulfur; and
(c) a compound of the formula

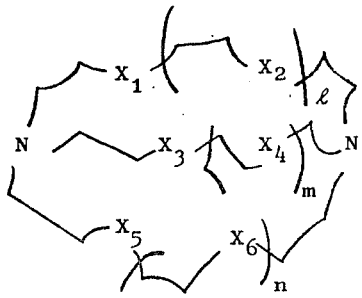

wherein $X_1$, $X_2$, $X_3$, $X_4$, $X_5$, and $X_6$ each represent oxygen, sulfur, or R–N in which R represents an alkyl group having from 1 to 5 carbon atoms, and $l$, $m$, and $n$ each represent an integer from 1 to 5.

20. The process of claim 16 wherein the mixture contains at least one of the dimers (IIA)$_t$ and (IIA)$_c$ and the heating of the mixture is carried out a temperature of about from 40° C to 70° C.

21. The process of claim 6 wherein the mixture contains at least one of the trimers (IIIA) and (IIIB) and the heating of the mixture is carried out at a temperature of about from 60° C to 100° C.

22. The process of claim 12 wherein the alkali metal fluoride is present in an amount ranging from about 0.1 to 10 mols/liter based on the non-protonic polar solvent, and the crown ether is present in an amount of at least 2 mol% based on the alkali metal fluoride.

23. The process of claim 12 wherein the heating of the mixture is carried out at atmospheric pressure.

24. The process of claim 16 wherein the heating of the mixture is carried out at a pressure above atmospheric but below about 10 kg/cm² in gage pressure.

25. A process of converting an oligomer of hexafluoropropene into a thermodynamically stable isomer thereof comprising:
(A) preparing a mixture containing
(1) a non-protonic polar solvent selected from the group consisting of acetonitrile, N,N-dimethylformamide, and dimethyl sulfoxide;

(2) an alkali metal fluoride selected from the group consisting of potassium fluoride and cesium fluoride;

(3) a crown ether selected from a group consisting of
  (a) a polycyclic ether selected from the group consisting of 18-crown-6, benzo-15-crown-5, dibenzo-18-crown-6, dicyclohexyl-18-crown-6, decalyl-15-crown-5, dibenzo-14-crown-4, dibenzo-20-crown-4, dibenzo-18-crown-5, and dibenzo-26-crown-6;
  (b) the polycyclic ethers of (a) above, in which the oxygen atoms have been at least partially replaced by sulfur; and
  (c) a compound of the formula

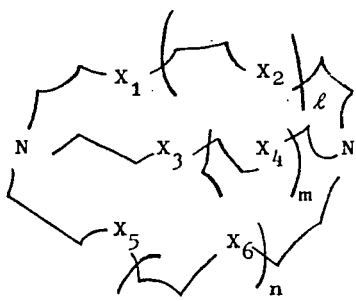

wherein $X_1$, $X_2$, $X_3$, $X_4$, $X_5$, and $X_6$ each represent oxygen, sulfur, or R-N in which R represents an alkyl group having from 1 to 5 carbon atoms, and $l$, $m$, and $n$ each represent an integer from 1 to 5; and (4) at least one member selected from the group consisting of dimer (IIA)$_t$ having the formula

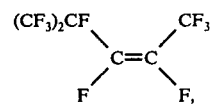

dimer (IIA)$_c$ having the formula

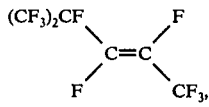

trimer (IIIa) having the formula

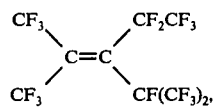

and trimer (IIIB) having the formula

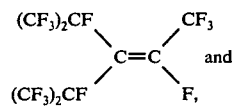

(B) heating the mixture at a temperature of about from 20° C to 150° C, whereby dimers (IIA)$_t$ and (IIA)$_c$, where present, are each converted into the thermodynamically stable dimeric isomer (IIB) having the formula

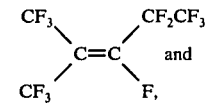

trimer (IIIA) and (IIIB), where present, are respectively converted into the thermodynamically stable trimeric isomers (IIIC)$_a$ and (IIIC)$_b$ having the respective formulas

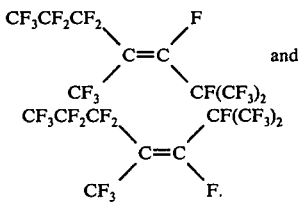

* * * * *